United States Patent [19]

Hahn

[11] Patent Number: 4,884,568

[45] Date of Patent: Dec. 5, 1989

[54] RADIATION COAGULATOR

[75] Inventor: Andreas Hahn, Sauerlach, Fed. Rep. of Germany

[73] Assignee: Messerschmitt-Bölkow-Blohm GmbH, Munich, Fed. Rep. of Germany

[21] Appl. No.: 202,146

[22] Filed: Jun. 3, 1988

[30] Foreign Application Priority Data

Jul. 14, 1987 [DE] Fed. Rep. of Germany ....... 3723227

[51] Int. Cl.$^4$ .............................................. A61B 17/36
[52] U.S. Cl. .................................. 128/303.1; 128/397
[58] Field of Search ....................... 128/303.1, 395–398

[56] References Cited

U.S. PATENT DOCUMENTS

| | | | |
|---|---|---|---|
| 3,467,098 | 9/1969 | Ayres | 128/303.1 |
| 4,233,493 | 11/1980 | Nath | 128/397 |
| 4,273,130 | 1/1981 | Enderby | 128/303.1 |
| 4,646,737 | 3/1987 | Hussein et al. | 128/303.1 |
| 4,681,104 | 7/1987 | Edelman | 128/303.1 |
| 4,719,914 | 1/1988 | Johnson | 128/303.1 |
| 4,807,596 | 2/1989 | Hochberger et al. | 128/303.1 |

FOREIGN PATENT DOCUMENTS

| | | | |
|---|---|---|---|
| 2846471 | 5/1980 | Fed. Rep. of Germany | 128/303.1 |
| 2458279 | 2/1981 | France | 128/395 |
| 0787044 | 12/1980 | U.S.S.R. | 128/397 |

Primary Examiner—Max Hindenburg
Attorney, Agent, or Firm—Kenyon & Kenyon

[57] ABSTRACT

A radiation coagulator with a radiation source which has a large infrared content and with a sleeve-shaped cap which is placed on the holding tube at the radiation exit end of the light conductor, and with which the area of the tissue to be coagulated is brought into contact.

6 Claims, 1 Drawing Sheet

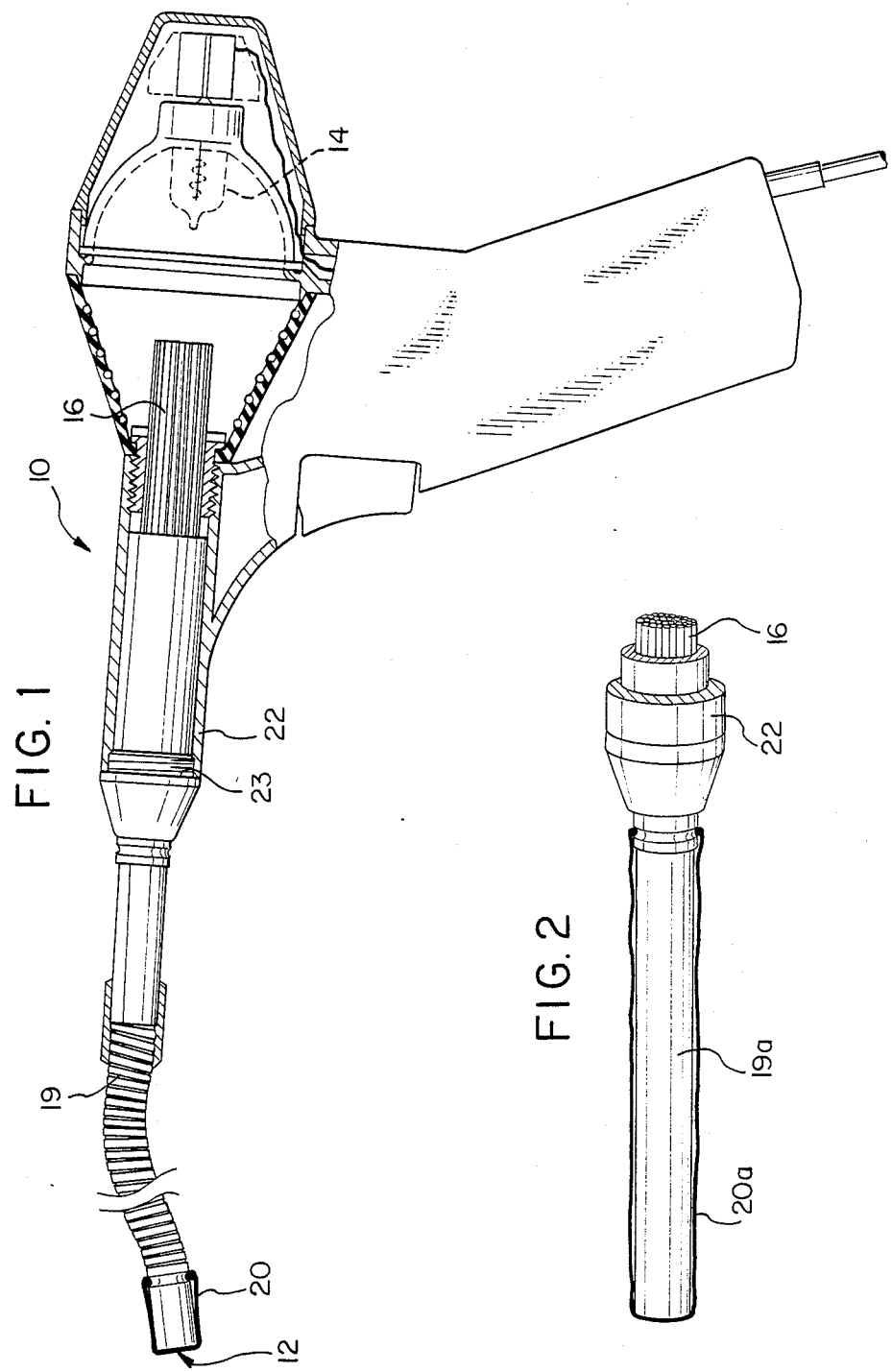

RADIATION COAGULATOR

BACKGROUND OF THE INVENTION

The present invention relates to a radiation coagulator with a radiation source which has a large infrared content, with a light conductor attached to a holding tube and with a sleeve-like cap which is placed on the holding tube at the radiation exit end of the light conductor and which is brought into contact with the point of the tissue to be coagulated.

Such a radiation coagulator is known, for instance, from U.S. Pat. No. 4,233,493.

This known radiation coagulator is distinguished by the combination of a tungsten-halogen lamp as the radiation source, a rigid light conductor rod placed in a holding tube of fused quartz and a contact element which is designed as a sleeve-like cap and is placed at the radiation exit end of the light conducting rod on the holding tube, and the light exit surface of which is coated with a thin smooth layer of perfluoroethylenepropylene or polytetrafluoroethylene with perfluoroalcoxy side chains.

This known radiation coagulator has a number of disadvantages.

For one, the use of perfluoroethylenepropylene or polytetrafluoroethylene is not without danger since such compounds separate toxic fluorine compounds when overheated. It needs no detailed explanation that this is extremely problematical in the treatment of open wounds, etc.

In addition, the handling and processing of such compounds is not without problems. It is furthermore possible only with difficulty to process these compounds by injection molding techniques so that according to this patent already no integral contact element is provided, but a contact element, the light exit surface of which is coated with just these compounds and therefore has a "multi-part design. This design, however, has the disadvantage that it makes sterilizing the contact element more difficult.

It should be mentioned as a further substantial disadvantage of the known radiation coagulator that the design does not permit flexible matching to various treatment methods. Particularly the light conductor designed as a rigid light conductor rod can make the equipment difficult to handle and prevents treatment at inaccessible points.

DE-OS 31 13 869 describes an endoscope with a device for irradiating tissue points with laser light which has a flexible holding tube in the form of a hose, in which the optical fibers are arranged.

Finally, a laser coagulator is known from U.S. Pat. No. 4,646,737 which comprises a sleeve-shaped cap which is arranged at the light exit end of the light conductor, converts the laser radiation into heat, is made of metal or ceramics and is snapped onto the holding tube.

SUMMARY OF THE INVENTION

It is an object of the present invention to provide a radiation coagulator such that it is not only producible simply, but is also easy to handle during treatments. In particular, the radiation coagulator should not be dangerous also when overheated and should be readily adaptable to different treatment methods.

The above and other objects of the present invention are achieved by a radiation coagulator with a radiation source which has a large infrared content, having a light conductor mounted in a holding tube and a sleeve-like cap which is placed at the radiation exit end of the light conductor on the holding tube, with which a spot of tissue to be coagulated is brought into contact, the light conductor comprising a bundle of individual fibers, the holding tube being flexible, the sleeve-like cap being snapped onto the holding tube, at least the region of the sleeve-like cap which comes into contact with the tissue spot to be coagulated comprising silicone rubber.

The design of the sleeve according to the invention as a snap-on element makes possible the use of a flexible holding tube into which the light conductor consisting of a bundle of individual fibers is built. It is of particular advantage here that at least the contact region of the sleeve consists of silicone rubber. This facilitates, for one, the production so that also comparatively complicated sleeve shapes can be produced, for instance, by an injection molding process. Above all, however, silicone rubber has the advantage that it liberates no toxic compounds also when overheated.

BRIEF DESCRIPTION OF THE DRAWINGS

The invention will be described in greater detail in the following detailed description with reference to the drawing figures in which:

FIG. 1 shows a side view of the invention; and

FIG. 2 shows a detail of part of the device shown in FIG. 1.

DETAILED DESCRIPTION

The design according to the invention makes it possible in a particular manner to make the light conductor interchangeable and to thus employ a multiplicity of different light conductors which are adapted to the respective problem. For instance, the light conductor can be in a manner known per se as a rigid light conductor such as is used, for instance, for treating open wounds at readily accessible main parts. It is possible thereby that the light conductor is adapted to the body shape of the patient at points which are difficult to reach during the treatment.

FIG. 1 shows a radiation coagulator 10 having a light exit 12. The light is provided by a radiation source 14 to a plurality of optical fibers 16 and transmitted to the exit 12. The fiber bundle may be flexible, as shown in FIG. 1, covered by a flexible spiral holding tube 19 or a flexible solid holding tube 19a as shown in FIG. 2. As shown, a sleeve 20, 20a is provided covering the flexible holding tube. The sleeve may cover only a part of the holding tube (FIG. 1), or it may cover the entire length of the holding tube (FIG. 2). The holding tube may be bolted to the coagulator housing 22 by screw means 23 or be fastened by any other suitable means.

The sleeve may consist in part of silicone rubber, but in a preferred embodiment, completely of silicone rubber. This design makes it possible to pull off the sleeve as a whole to sterilize it or to replace it by a sterilized or "disposable" sleeve.

It is further preferred if not only parts of the light conductor and/or the sleeve, but also the housing of the radiation source consist of silicone rubber.

From DE-OS 25 11 037 it is known that the shielding housing consists of a polymer or copolymer built-up mainly from the chemical elements C and F to which pigment is added which absorbs radiation in the blue and green spectral region. Such a solution has the disadvantage that as a rule pigments with a cadmium base must be used which are toxic. Upon overheating, as may happen, this is a disadvantage particularly in a handguided radiation coagulator. The silicone rubber housing can contain, like the remaining silicone rubber parts, for increasing the stiffness, a metal spiral or other metal support parts, with the exception of the light exit window.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. A radiation coagulator having a radiation source which has a large infrared content disposed in a coagulator housing, further having a light conductor mounted in a holding tube attached to the housing and having a sleeve-like cap which is placed at the radiation exit end of the light conductor on the holding tube, with which cap a spot of tissue to be coagulated is brought into contact, and further wherein:

the light conductor comprises a bundle of individual fibers;

the holding tube is flexible;

the sleeve-like cap is snapped onto the holding tube;

and at least the region of the sleeve-like cap which comes into contact with the tissue spot to be coagulated comprises silicone rubber, said sleeve-like cap having a light exit window also comprising said silicone rubber.

2. The radiation coagulator recited in claim 1, wherein the holding tube reeiving the light conductor is bolted to the coagulator housing.

3. The radiation coagulator recited in claim 1, wherein the sleeve-like cap comprises completely of silicone rubber.

4. The radiation coagulator recited in claim 1 wherein the holding tube receiving the light conductor is surrounded by silicone rubber at least in its forward part, but preferably over the entire length.

5. The radiation coagulator recited in claim 1, wherein the housing of the radiation source comprises silicone rubber.

6. The radiation coagulator recited in claim 1, wherein metal support parts are provided in the silicone rubber sleeve-like cap with the exception of the light exit window of said sleeve-like cap.

* * * * *